United States Patent
Ganguly et al.

(10) Patent No.: US 6,277,830 B1
(45) Date of Patent: Aug. 21, 2001

(54) 5'-AMINO ACID ESTERS OF RIBAVIRIN AND THE USE OF SAME TO TREAT HEPATITIS C WITH INTERFERON

(75) Inventors: Ashit K. Ganguly, Upper Montclair; Jinping McCormick, Edison; Raymond G. Lovey, West Caldwell; Frank Bennett, Piscataway; Anil K. Saksena, Upper Montclair; Viyyoor M. Girijavallabhan, Parsippany, all of NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 09/348,534

(22) Filed: Jul. 7, 1999

Related U.S. Application Data

(63) Continuation-in-part of application No. 09/174,059, filed on Oct. 16, 1998, now abandoned.

(51) Int. Cl.[7] .................................................. A01N 43/04
(52) U.S. Cl. .................. 514/43; 514/2; 514/21; 514/894; 424/85.4; 424/85.7; 530/351
(58) Field of Search ................................. 514/43, 894, 21, 514/2; 424/85.7, 85.4; 530/351

(56) References Cited

U.S. PATENT DOCUMENTS

| | | | |
|---|---|---|---|
| 4,211,771 | 7/1980 | Witkowski | 536/23 |
| 4,925,930 | 5/1990 | Robins et al. | 536/23 |
| 5,503,828 | * 4/1996 | Testa et al. | 424/85.7 |
| 5,998,605 | * 12/1999 | Chamberlain et al. | 536/27.11 |

FOREIGN PATENT DOCUMENTS

| | | |
|---|---|---|
| 2511828 | 10/1975 | (DE) . |
| 0 090 405 | 10/1983 | (EP) . |
| 707855A2 | * 4/1996 | (EP) . |
| 0 707 855 A2 | 4/1996 | (EP) . |
| 0 707 855 A3 | 4/1996 | (EP) . |
| WO 94/22887 | 10/1994 | (WO) . |
| WO 98/21223 | 5/1998 | (WO) . |

OTHER PUBLICATIONS

Zakharieva et al., Bioorg & Med Chem Letts, vol. 4, No. 24, pp. 2831–2832, Dec. 22, 1994.*
Reichard, et al., *The Lancet,* 1998, vol. 351, pp. 83–87.
Poynard, et al., *The Lancet,* 1998, vol. 352, pp. 1426–1432.
McHutchinson, et al., *N. Eng. J. Med.,* 1998, vol. 339, pp. 1485–1492.
Davis, et al., *N. Eng. J. Med.,* 1998, vol. 339, pp. 1493–1499.
Brissot, *Gastroenierol Clin. Biol.,* 1997, vol. 20, ppS89–S95.

* cited by examiner

Primary Examiner—James O. Wilson
(74) Attorney, Agent, or Firm—Thomas D. Hoffman

(57) ABSTRACT

5'-Amino acid esters of ribavirin represented by formula I:

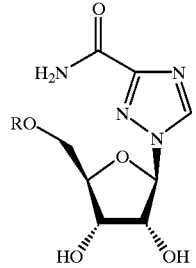

wherein R is $CH_3CH(NH_2)—CO—$, $CH_3CH_2(CH_3)CHCH(NH_2)—CO—$ or $H_2N(CH_2)_4CH(NH_2)—CO—$; preferably R is

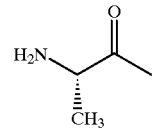

or a pharmaceutically acceptable salt thereof, e.g., trifluoroacetate, tosylate, mesylate, and chloride, pharmaceutical compositions containing them as well as methods of treating patients having susceptible viral infections, e.g., chronic hepatitis C infections by administering a therapeutically effective amount of a ribavirin derivative, alone or in combination with a therapeutically effective amount of interferon-alpha are disclosed.

43 Claims, No Drawings

5'-AMINO ACID ESTERS OF RIBAVIRIN AND THE USE OF SAME TO TREAT HEPATITIS C WITH INTERFERON

CROSS-REFERENCE TO RELATED APLLICATION

This application is a continuation-in-part of Ser. No. 09/174,059, filed Oct. 16, 1998, now abandoned.

BACKGROUND OF THE INVENTION

The present invention relates to 5'-amino acid esters of ribavirin represented by formula I:

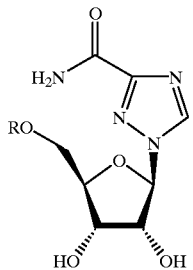

pharmaceutical compositions containing them as well as methods of treating patients having susceptible viral infections, e.g., chronic hepatitis C infections by administering a therapeutically effective amount of an amino acid ester of ribavirin represented by formula I, alone, or in combination with a therapeutically effective amount of interferon-alpha.

Chronic infection with hepatitis C virus ("HCV") is an insidious and slow-progressing disease having a significant impact on the quality of life. It can eventually result in cirrhosis of the liver, decompensated liver disease and/or hepatocelluar carcinoma.

Combination treatment with interferon alfa-2b and ribavirin of patients with chronic hepatitis C is disclosed by Reichard et al.(The Lancet 1998; 351;83–87; and T. Poynard et al.( The Lancet, 1998, Vol. 352, Oct. 31, p 1426–1432). See also J. G. McHutchinson et al. (N. Engl. J. Med.,1998, 339:1485–1492); and G. L. Davis et al. (N. Engl. J. Med., 1998, 339:1493–1499). However, this combination therapy is not always effective due to side effects associated ribavirin such as ribavirin-related hemolysis, and anemia.

There is a definite need for more potent, safer ribavirin derivatives having fewer side effects for use as monotherapy or in combination with antiviral agents, e.g., interferon-alpha, to treat patients having susceptible viral infections, e.g., chronic hepatitis C infections, in a long-term, effective manner.

SUMMARY OF THE INVENTION

The present invention provides a compound represented by the formula I:

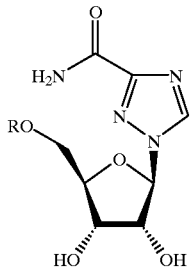

wherein R is $CH_3CH(NH_2)$—CO—, $CH_3CH_2(CH_3)CHCH(NH_2)$—CO— or $H_2N(CH_2)_4CH(NH_2)$—CO—;

or a pharmaceutically acceptable salt thereof.

The present invention also provides pharmaceutical compositions for treating susceptible viral infections comprising a compound of formula I and at least one pharmaceutically acceptable carrier.

The present invention also provides a method of treating a patient with a susceptible viral infection which comprises administering to said patient an effective amount of a compound of formula I.

The present invention also provides a method of treating a patient infected with chronic hepatitis C which comprises administering to said patient an effective amount of a compound of formula I in association with an effective amount of an interferon alfa for a time sufficient to eradicate detectable HCV-RNA levels, wherein the compound represented by the formula I:

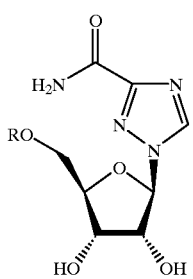

wherein R is $CH_3CH(NH_2)$—CO—, $CH_3,CH_2(CH_3)CHCH(NH_2)$—CO—or $H_2N(CH_2)_4CH(NH_2)$p—CO—; or a pharmaceutically acceptable salt thereof.

The present invention also provides a method of treating a patient infected with chronic hepatitis C which comprises administering to said patient an effective amount of a compound of formula II:

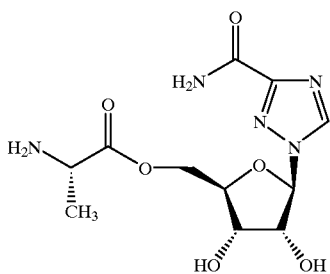

or a pharmaceutically acceptable salt thereof, in association with an effective amount of an interferon alfa for a time sufficient to eradicate detectable HCV-RNA levels.

DETAILED DESCRIPTION

The compounds of formula I metabolize in vivo into ribavirin and are useful for treating susceptible viral infections treatable with ribavirin, alone, or in combination with other ant-viral therapies eg., interferon-alfa, and so-called Highly Active Antiretroviral Therapy ("HAART". A-M. Vandamme et al., *Antiviral Chemistry & Chemotherapy*, 9:187–203 (1998) disclose current clinical treatments of HIV-1 infections in man including at least triple drug combinations or so-called Highly Active Antiretroviral Therapy ("HAART") ; HAART involves various combinations of nucleoside reverse transcriptase inhibitors ("NRTI"), non-nucleoside reverse transcriptase inhibitors ("NNRTI") and HIV protease inhibitors ("PI"). The treating of patients having chronic hepatitis C with the compounds of formula I is performed as part of a combination therapy with interferon-alfa, including interferon alfa-2a, interferon alfa-2b, consensus interferon especially interferon alfa-2b as well as pegylatyed interferon alfa-2a and pegylatyed interferon alfa-2b.

The present invention provides methods and pharmaceutical compositions containing a compound of formula I for treating susceptible viral infections, especially hepatitis C viral infections.

The term "susceptible viral infections" as used herein means viral infections caused by a wide range of RNA and DNA viruses, including, but not limited to, orthomyxoviruses, paramyxoviruses, arenaviruses, bunyaviruses, herpes viruses, adenoviruses, poxviruses, and retroviruses.

Typical suitable "susceptible viral infections" include influenza A and B viral infections; parainfluenza viral infections, respiratory syncytial virus("RSV") infections such as RSV bronchiolitis and RSV pneumonia especially such RSV infections in children and infants as well as RSV pneumonia in patients with preexisting cardiopulmonary disease, measles viral infections, Lassa fever viral infections, Korean Haemorrhagic fever infections, hepatitis B viral (HBV) infections, Crimean-Congo-Haemorrhagic and HCV infections and HIV-1 infections as well as viral infections found in immunocompromised patients. Other susceptible viral infections are disclosed in U.S. Pat. No. 4,211,771 at column 2, line 21 to column 3 line 37; doses and dose regimens and formulations are disclosed at column 3, line 4 to column 9, line 5; see also Canadian Patent No. 1,261,265. Sidwell, R. W., et al. Pharmacol. Ther., 1979, Vol 6 pp 123–146 discloses that the in vivo antiviral experiments conducted with ribavirin generally confirm one broad-spectrum antiviral activity seen in vitro and states that the efficacy of ribavirin is quite dependent upon the site of infection; the manner of treatment; the age of the animal and the virus dosage utilized. Tables 4 and 5 on page 127 list the RNA and DNA virus infections significantly inhibited in vivo by ribavirin.

The in vitro inhibitory concentrations of ribavirin are disclosed in Goodman & Gilman's *"The Pharmacological Basis of Therapeutics"*, Ninth Edition, (1996) McGraw Hill, NY, at pages 1214–1215. The Virazole product information discloses a dose of 20 mg/mL of Virazole aerosol for 18 hours exposure in the 1999 Physicians Desk Reference at pages 1382–1384.

Ribavirin dosage and dosage regimens are also disclosed by Sidwell, R. W., et al. Pharmacol. Ther 1979 Vol 6. pp23–146 in section 2.2 pp 126–130. Fernandes, H., et al., Eur. J. Epidemiol., 1986, Vol 2(1) pp1–14 at pages 4–9 disclose dosage and dosage regimens for oral, parenteral and aerosol administration of ribavirin in various preclinical and clinical studies.

The term "patients having hepatitis C infections" as used herein means any patient-including a pediatric patient- having hepatitis C and includes treatment-naive patients having hepatitis C infections and treatment-experienced patients having hepatitis C infections as well as those pediatric, treatment-naive and treatment-experienced patients having chronic hepatitis C infections.

These patients having hepatitis C include those who are infected with multiple HCV genotypes including type 1 as well as those infected with, e.g., HCV genotypes 2, 3, 4, 5 and/or 6 and other possible HCV genotypes.

The term "treatment-naive patients having hepatitis C infections" as used herein means patients with hepatitis C who have never been treated with ribavirin or any interferon, including but not limited to interferon-alfa, or pegylated interferon alfa.

The term "treatment-experienced patients having hepatitis C infections" as used herein means patients with hepatitis C who have been treated with ribavirin or any interferon, including but not limited to interferon-alfa, or pegylated interferon alfa, including relapsers and non-responder.

The term "relapsers" as used herein means treatment-experienced patients with hepatitis C who have relapsed after initial response to previous treatment with interferon alone, or in combination with ribavirin.

The term "non-responders" as used herein means treatment-experienced patients with hepatitis C who have not responded to prior treatment with any interferon alone, or in combination with ribavirin.

When the pegylated interferon-alfa administered is a pegylated interferon alfa-2b, the therapeutically effective amount of pegylated interferon alfa-2b administered during the treatment in accordance with the present invention, including in first and second treatment time periods, is in the range of about 0.1 to 9.0 micrograms per kilogram of pegylated interferon alfa-2b administered per week, in single or divided doses, preferably once a week (QW) or twice a week(BIW), preferably in the range of about 0.1 to about 9.0 micrograms per kilogram of pegylated interferon alfa-2b administered once a week (QW) or in the range of about 0.05 to about 4.5 micrograms per kilogram of pegylated interferon alfa-2b administered twice a week(BIW), or is in the range of about 0.5 to about 3.0 micrograms per kilogram of pegylated interferon alfa-2b administered per week, preferably in the range of about 0.5 to about 3.0 micrograms per kilogram of pegylated interferon alfa-2b administered once a week (QW) or in the range of about 0.25 to about 1.5 micrograms per kilogram of pegylated interferon alfa-2b administered twice a week, or is in the range of about 0.75 to about 1.5 micrograms per kilogram of pegylated interferon alfa-2b administered per week, most preferably is in the range of about 0.75 to about 1.5 micrograms per kilogram of pegylated interferon alfa-2b administered once a week or about 0.375 to about 0.75 micrograms per kilogram of pegylated interferon alfa-2b administered twice a week.

When the pegylated interferon-alfa administered to pediatric patients is a pegylated interferon alfa-2b, the therapeutically effective amount of pegylated interferon alfa-2b administered during the treatment in accordance with the present invention is in the range of about 0.1 to 9.0 micrograms per kilogram of pegylated interferon alfa-2b administered per week, in single or divided doses, preferably once a week (QW) or twice a week(BIW), more preferably about 0.1 to about 9.0 micrograms per kilogram of pegylated interferon alfa-2b administered once a week (QW), or about 0.05 to about 4.5 micrograms per kilogram of pegylated interferon alfa-2b administered per week, in single or divided doses, preferably once a week (QW) or twice a week(BIW), more preferably about 0.05 to about 4.5 micrograms per kilogram of pegylated interferon alfa-2b administered once a week, or preferably about 0.75 to about 3.0 micrograms per kilogram of pegylated interferon alfa-2b administered in single or divided doses, preferably once a week (QW) or twice a week(BIW), more preferably about 0.75 to about 3.0 micrograms per kilogram of pegylated interferon alfa-2b administered once a week or about 0.375 to about 1.5 micrograms per kilogram of pegylated interferon alfa-2b administered twice a week, and most preferably about 2.25 to about 2.6 micrograms per kilogram of pegylated interferon alfa-2b administered once a week or about 1.1 to about 1.3 micrograms per kilogram of pegylated interferon alfa-2b administered twice a week(BIW).

When the pegylated interferon-alfa administered is a pegylated interferon alfa-2a, the therapeutically effective amount of pegylated interferon alfa-2a administered in accordance with the present invention, is in the range of about 50 micrograms to about 500 micrograms once a week("QW"), preferably about 150 micrograms to about 250 micrograms QW or the effective amount is in the range of about 50 micrograms to about 250 micrograms twice a week, preferably about 100 micrograms to about 125 micrograms twice a week.

When the pegylated interferon-alfa administered to a pediatric patient is a pegylated interferon alfa-2a, the therapeutically effective amount of pegylated interferon alfa-2a administered in accordance with the present invention, is in the range of about 50 micrograms to about 500 micrograms once a week("QW"), preferably about 300 micrograms to about 375 micrograms QW or the therapeutically effective amount of pegylated interferon alfa-2a administered to a pediatric patient is in the range of about 50 micrograms to about 250 micrograms twice a week, preferably about 150 micrograms to about 190 micrograms once a week The 5'-amino acid esters of ribavirin represented by formula I is administered to the patient having chronic HCV in association with pegylated interferon-alfa, that is, before, after or concurrently with the administration of the pegylated interferon alfa. The pegylated interferon-alfa dose is preferably administered during the same period of time that the patient receives doses of 5'-amino acid esters of ribavirin represented by formula I. The amount of 5'-amino acid esters of ribavirin represented by formula I administered concurrently with the pegylated interferon-alfa is from about 200 to about 1600 mg per day, preferably about 300 to about 1200 mg/day or about 400 to about 800 mg day and most preferably about 400 to about 600 mg a day. The pegylated interferon-alfa dose is also preferably administered to the pediatric patient during the same period of time that such patient receives doses of the 5'-amino acid esters of ribavirin represented by formula I . The amount of the 5'-amino acid esters of ribavirin represented by formula I administered to the pediatric patient having chronic HCV concurrently with the pegylated interferon-alfa is from about 4 to about 15 mg per kilogram per day, preferably about 4, 6 or 8 mg per kilogram per day, in divided doses.

Pegylated interferon-alfa formulations are not effective when administered orally, so the preferred method of administering the pegylated interferon-alfa is parenterally, preferably by sub-cutaneous(SC), intravenous(IV), or intramuscular(lM) injection. The 5'-amino acid esters of ribavirin represented by formula I may be administered orally in capsule, tablet, or liquid form, intranasally as an aerosol by nasal spray or parenterally, preferably by SC, IV, or IM injection. The 5'-amino acid esters of ribavirin represented by formula I may be orally administered in association with the parenteral administration of pegylated interferon-alfa . Of course, other types of administration of both medicaments, as they become available, are contemplated, such as transdermally, by suppository, by sustained release dosage form, and by pulmonary inhalation. Any form of administration will work so long as the proper dosages are delivered without destroying the active ingredient The term "interferon-alfa" as used herein means the family of highly homologous species-specific proteins that inhibit viral replication and cellular proliferation and modulate immune response. Typical suitable interferon-alfas include, but are not limited to, recombinant interferon alfa-2b, such as lntron-A interferon available from Schering Corporation, Kenilworth, N.J., recombinant interferon alfa-2a, such as Roferon interferon available from Hoffmann-La Roche, Nutley, N.J., recombinant interferon alpha-2c, such as Berofor alpha 2 interferon available from Boehringer Ingelheim Pharmaceutical, Inc., Ridgefield, Conn., interferon alpha-n1, a purified blend of natural alfa interferons, such as Sumiferon available from Sumitomo, Japan or as Wellferon interferon alpha-n1 (INS) available from the Glaxo-Wellcome Ltd., London, Great Britain, or a consensus alpha interferon, such as those described in U.S. Pat. Nos. 4,897,471 and 4,695,623 (especially Examples 7, 8 or 9 thereof) and the specific product available from Amgen, Inc., Newbury Park, Calif., or interferon alfa-n3 a mixture of natural alfa interferons made by Interferon Sciences and available from the Purdue Frederick Co., Norwalk, Conn., under the Alferon Tradename. The use of interferon alfa-2a or alpha 2b is preferred. Since interferon alpha 2b, among all interferons, has the broadest approval throughout the world for treating chronic hepatitis C infection, it is most preferred. The manufacture of interferon alpha 2b is described in U.S. Pat. No. 4,530,901.

The term "pegylated interferon alfa" as used herein means polyethylene glycol modified conjugates of interferon alfa, preferably interferon alfa-2a and -2b. The preferred polyethylene-glycol-interferon alfa -2b conjugate is $PEG_{12000}$-interferon alfa 2b. The phrases "12,000 molecular weight polyethylene glycol conjugated interferon alpha" and "$PEG_{12000}$-IFN alfa" as used herein mean conjugates such as are prepared according to the methods of International Application No. WO 95/13090 and containing urethane linkages between the interferon alfa-2a or -2b amino groups and polyethylene glycol having an average molecular weight of 12000.

The preferred PEG$_{12000}$-interferon alfa-2b is prepared by attaching a PEG polymer to the epsilon amino group of a lysine residue in the IFN alfa-2b molecule. A single PEG$_{12000}$ molecule is conjugated to free amino groups on an IFN alfa-2b molecule via a urethane linkage. This conjugate is characterized by the molecular weight of PEG$_{12000}$ attached. The PEG12000-IFN alfa-2b conjugate is formulated as a lyophilized powder for injection. The objective of conjugation of IFN alfa with PEG is to improve the delivery of the protein by significantly prolonging its plasma half-life, and thereby provide protracted activity of IFN alfa.

Other pegylated interferon alfa conjugates can be prepared by coupling an interferon alfa to a water-soluble polymer. A non-limiting list of such polymers include other polyalkylene oxide homopolymers such as polypropylene glycols, polyoxyethylenated polyols, copolymers thereof and block copolymers thereof. As an alternative to polyalkylene oxide-based polymers, effectively non-antigenic materials such as dextran, polyvinylpyrrolidones, polyacrylamides, polyvinyl alcohols, carbohydrate-based polymers and the like can be used. Such interferon alfa-polymer conjugates are described in U.S. Pat. No. 4,766,106, U.S. Pat. No. 4,917,888, European Patent Application No. 0 236 987, European Patent Application Nos. 0510 356, 0 593 868 and 0 809 996 (pegylated interferon alfa-2a) and International Publication No. WO 95/13090.

Pharmaceutical composition of pegylated interferon alfa suitable for parenteral administration may be formulated with a suitable buffer, e.g., Tris-HCI, acetate or phosphate such as dibasic sodium phosphate/monobasic sodium phosphate buffer, and pharmaceutically acceptable excipients, e.g., sucrose, carriers, e.g., humanor recombinant plasma albumin, tonicity agents, e.g. NaCI, preservatives, e.g., thimerosol, cresol or benyl alcohol, and surfactants, e.g., tweens or polysorabates in sterile water for injection. The pegylated interferon alfa- may be stored as lyophilized powders under a refrigeration at 2°–8° C. The reconstituted aqueous solutions are stable when stored between 2° and 8° C. and used within 24 hours of reconstitution. See for example U.S. Pat. Nos, 4,492,537; 5,762,923 and 5,766,582. The reconstituted aqueous solutions may also be stored in prefilled, multi-dose syringes such as those useful for delivery of drugs such as insulin. Typical suitable syringes include systems comprising a prefilled vial attached to a pen-type syringe such as the NOVOLET Novo Pen available from Novo Nordisk, as well as prefilled, pen-type syringes which allow easy self-injection by the user. Other syringe systems include a pen-type syringe comprising a glass cartridge containing a diluent and lyophilized pegylated interferon alfa powder in a separate compartment.

A person suffering from chronic hepatitis C infection may exhibit one or more of the following signs or symptoms:

(a) elevated ALT, (b) positive test for anti-HCV antibodies, (c) presence of HCV as demonstrated by a positive test for the presence of HCV-RNA in the serum, (d) clinical stigmata of chronic liver disease, (e) hepatocelluar damage.

The combination therapy of pegylated interferon-alfa and the 5'-amino acid esters of ribavirin represented by formula I may also be administered in association with anti-retroviral therapy,e.g., HAART, to the patient co-infected with the HIV-1 and HCV infection and exhibiting one or more of the above signs or symptoms in amounts sufficient to eliminate or at least alleviate one or more of the signs or symptoms of the HCV infection, and to lower the HIV-1-RNA and HCV-RNA serum levels each by at least a power of ten, and preferably to eradicate detectable HCV-RNA at least by the end of about 20 to about 50 weeks, preferably at least 24 weeks to 48 weeks and to maintain no detectable HCV-RNA for at least 24 weeks after the end of the about 20 to about 50 weeks. Administration of the 5'-amino acid esters of ribavirin represented by formula I may be discontinued after the end of the second time period depending upon the judgment of the attending clinician.

The term "no detectable HCV-RNA" in the context of the present invention means that there are fewer than 100 copies of HCV-RNA per ml of serum of the patient as measured by quantitative, multi-cycle reverse transcriptase PCR methodology. HCV-RNA is preferably measured in the present invention by research-based RT-PCR methodology well known to the skilled clinician. This methodology is referred to herein as HCV-RNA/qPCR. The lower limit of detection of HCV-RNA is 100 copies/mL. Serum HCV-RNA/qPCR testing and HCV genotype testing will be performed by a central laboratory. See also J. G. McHutchinson et al. (N. Engl. J. Med., 1998, 339:1485–1492), and G. L. Davis et al. (N. Engl. J. Med. 339:1493–1499).

In a preferred embodiment of the present invention, those patients co-infected with HIV-1 and HCV infections are treated with pegylated interferon alfa in combination with the 5'-amino acid esters of ribavirin represented by formula I and a HAART combination considered appropriate by the attending clinician and the patient. See also J. G. McHutchinson et al. (N. Engl. J. Med., 1998, 339:1485–1492), and G. L. Davis et al. (N. Engl. J. Med. 1998, 339:1493–1499).

Biological Activity

The compounds of formula I useful for treating patients having susceptible viral infections, e.g., chronic hepatitis C. The compounds of formula I metabolize in vivo into ribavirin and are useful for treating susceptible viral infections treatable with ribavirin, alone, or in combination with other anti-viral therapies, e.g., interferon-alfa and HAART. The treating of patients having chronic hepatitis C with the compounds of formula I is performed as part of a combination therapy with interferon-alfa, especially interferon alfa-2b.

Compounds of formula I metabolize in vivo into ribavirin and have produced higher plasma concentrations of ribavirin after oral administration of a compound of formula I to rats and monkeys compared to administration of ribavirin. The pharmacokinetics of the prefered compounds of formula I are presented in Tables 1 & 2

TABLE 1

Ribavirin Concentrations of Pooled Rat[1] Plasma (2 rats/pool) Following Oral Administration of 20 mpk Ribavirin Equivalent Amounts of Salts of the Compounds of Formula I in 20% Hydroxypropyl-beta-cyclodextrin(HPBCD)

| Compound[2] | AUC (pooled)[3] (ng.hr/mL) | C.V.[4] (%) | Conc. (6 hr) (ng/mL) | C.V.[4] (%) |
|---|---|---|---|---|
| A | 1238 | 81.4 | 152 | 30.5 |
| B | 2554 | 25.0 | 226 | 20.0 |
| C | 1011 | *** | 294 | — |
| D | 2043 | 1.4 | 173 | 67.3 |

[1] Male Sprague Dawely (CD) rats (N = 2) obtained from Charles River, Wilmington, MA 01887: Single dose, PO, (Fasted overnight); 20 mg/Kg (mpk) ribavirin equivalent PO dose of the compound of formula I in 20% HPBCD (w/v); Concentration: 4 mg/ml ribavirin equivalent and dosing volume: 5 ml/Kg.

[2] (a) Compound A is the compound of formula I wherein R is H, i.e. , ribavirin
(b) Compound B is the trifluoroacetate salt of the compound of formula I wherein R is [CF$_3$CO$_2^-$]L-CH$_3$CH$_{2(CH3)}$CHCH(NH$_3^{\oplus}$)—CO—.
(c) Compound C is the ditosylate salt of the compound of formula

TABLE 1-continued

Ribavirin Concentrations of Pooled Rat[1] Plasma (2 rats/pool) Following Oral Administration of 20 mpk Ribavirin Equivalent Amounts of Salts of the Compounds of Formula I in 20% Hydroxypropyl-beta-cyclodextrin(HPBCD)

I wherein R is 2[p-CH$_3$C$_6$H$_4$SO$_3^-$]L-H$_3$N$^\oplus$(CH$_2$)$_4$CH (NH$_3^\oplus$)—CO—.
(d) Compound D is the tosylate salt of the compound of formula I wherein R is [p-CH$_3$C$_6$H$_4$SO$_3^-$]L-CH$_3$CH(NH$_3^\oplus$)—CO—, i.e.,

H$_3^+$N—CH(CH$_3$)—C(=O)—  TSO$^-$

[3] Area under the curve measured from 0 to 6 hrs. after oral administration to 2 rats of an aqueous solution of compounds of formula I in 20% HPBCD.
[4] % CV is percent coefficient of variation which is a relative measure of variability. See Steele and Torrie, "Principles and Procedures of Statistics", (1980) 2nd Edition, McGraw-Hill, NY, at page 27.

TABLE 2

Ribavirin Concentrations of Pooled Cynomolgus Monkeys[1] Plasma (2 monkeys/pool) Following Oral Administration of 10 mpk of Ribavirin Equivalent Amounts of Salts of Compounds of Formula I Dissolved in 0.4% Methylcellulose(MC)

| Compound[2] | AUC (24)[3] (ng.hr/mL) | AUC(48 hr). (ng.hr/mL) | AUC(72 hr) (ng.hr/mL) | Cmax. (ng/mL) |
|---|---|---|---|---|
| A | 4013 | 5506 | 5902 | 398[4] |
| B | 4791 | 5749 | 5749 | 831[5] |
| C | 6033 | 8050 | 8381 | 661[6] |
| D | 9072 | 11632 | 12528 | 1012[7] |

[1] Non-naive male Cynomolgus monkeys (N = 2)
[2] (a) Compound A is the compound of formula I wherein R is H, i.e., ribavirin.
(b) Compound B is the trifluoroacetate salt of the compound of formula I wherein R is [CF$_3$CO$_2^-$]L-CH$_3$CH$_2$(CH$_3$)CHCH(NH$_3^\oplus$) —CO—.
(c) Compound C is the ditosylate salt of the compound of formula I wherein R is 2[p-CH$_3$C$_6$H$_4$SO$_3^-$]L-H$_3$N$^\oplus$(CH$_2$)$_4$CH (NH$_3^\oplus$—CO—
(d) Compound D is the tosylate saltof the compound of formula I wherein R is [p-CH$_3$C$_6$H$_4$SO$_3$]L-CH$_3$CH(NH$_3^\oplus$) —CO—, i.e.,

H$_3^+$N—CH(CH$_3$)—C(=O)—  TSO$^-$

[3] Area under the curve measured from 0 to 24, 48 or 72 hrs. after oral administration to non-naive male Cynomolgus monkeys of an oral gavage of a 0.4% MC solutions of the compounds of formula I at a target dose of 10 mg (free base)/Kg and at a target dose volume of 2 ml/kg..
[4] Tmax for A is 1.5 hrs.
[5] Tmax for B is 1.0 hrs.
[6] Tmax for C is 1.5 hrs.
[7] Tmax for D is 1.5 hrs The pharmaceutical compositions of the 5'-amino acid esters of ribavirin represented by formula I may be adapted for any mode of administration e.g., for oral, parenteral, e.g., subcutaneous ("SC"), intramuscular ("IM"), intravenous ("IV") and intraperitoneal ("IP"), topical or vaginal administration or by inhalation (orally or intranasally). Preferably the ribavirin compounds represented by formula I are administered orally.

Such compositions may be formulated by combining a compound formula I or an equivalent amount of a pharmaceutically acceptable of compound I with an suitable, inert, pharmaceutically acceptable carrier or diluent which may be either solid or liquid. The compounds of formula I are preferably converted into the pharmaceutically acceptable acid addition salts by adding to compounds of formula I an equivalent amount (or two equivalents in the case of the lysine ester) of a pharmaceutically acceptable acid. Typically suitable pharmaceutically acceptable acids include the mineral acids, e.g., HNO$_3$ H$_2$SO$_4$, H$_3$PO$_4$, HCl, HBr, organic acids, including, but not limited to, acetic, trifluoroacetic, propionic, lactic, maleic, succinic, tartaric, glucuronic and citric acids as well as alkyl or arylsulfonic acids, such as p-toluenesulfonic acid, 2-naphthalenesulfonic acid, or methanesulfonic acid. The preferred pharmaceutically acceptable salts are trifluoroacetate, tosylate, mesylate, and chloride.

Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration Examples of pharmaceutically acceptable carriers and methods of manufacture for various compositions may be found in A. Gennaro (ed.), Remington's Pharmaceutical Sciences, 18th Edition, (199), Mack Publishing Co., Easton, Pa.

Liquid form preparations include solutions, suspensions and emulsions. As an example may be mentioned water or water-propylene glycol solutions for parenteral injection.Solid form preparations may be converted into liquid preparations shortly before use for either oral or administration. Parenteral forms to be injected intravenously, intramuscularly or subcutaneously are usually in the form of sterile solutions and may contain tonicity agents (salts or glucose), and buffers. Opacifiers may be included in oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g., nitrogen.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound of formula I in a unit dose of preparation may be varied or adjusted from about 200 mg to about 1600 mg per day, preferably from about 300 mg to about 1200 mg per day, more preferably from about 400 mg to about 800 mg per day, and most preferably from about 400 mg to about 600 mg per day, in single or divided doses, according to the particular compound and particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. The dose of the compounds of formula I should be chosen to provide steady state plasma concentrations of ribavirin in the range of about 1000 to about 10,000 mg/mL, preferably in the range of about 1500 to about 5,000 mg/mL and more preferably in the range of about 2000 to about 4000 mg/mL. Plasma ribavirin concentrations may be determined using high pressure liquid chromatographic material with tandem mass spectrometric detection. The method was validated with respect to linearity, selectivity, precision, accuracy and has a limit of quantitation of 50 mg/mL. A typical recommended daily dosage regimen for oral administration can range from about 1 mg/kg/day to about 1000 mg/kg/day, in two to four divided doses.

The present invention concerns compounds represented by the formula I:

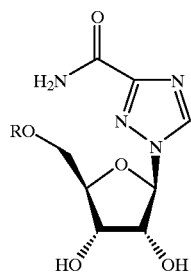

I wherein R is $CH_3CH(NH_2)$—CO—, $CH_3CH_2(CH_3)CHCH(NH_2)$—CO— or $H_2N(CH_2)_4CH(NH_2)$—CO—; or stereoisomers thereof, or a pharmaceutically acceptable salt thereof.

R may be $CH_3CH(NH_2)$—CO—, i.e., α-aminopropanoyl, in the form of a stereoisomeric mixture, i.e. the DL-form of α-aminopropanoyl—or
as one of the enantiomers, i.e.,
the L-form:

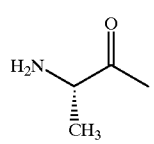

or D-form:

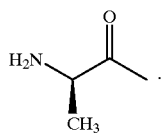

or mixtures thereof.

R may be $CH_3CH_2(CH_3)CHCH(NH_2)$—CO—, i.e., 2-amino-3-methylpentanoyl, (a) as a stereoisomeric mixture, i.e., the DL-Form-DL-(−+) erythro-2-amino-3-methylvaleroyl—of the formula:

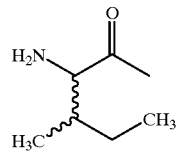

or (b) as one of the diastereomers of the formula, i.e., the L-allo- form of the formula:

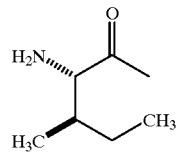

[(+)-threo-2-amino-3-methylpentanoyl]; or the L-form of the formula:

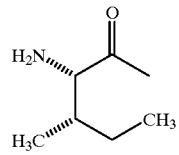

[L-(+)-amino-3-methylpentanoyk, or (2S,3S)-2-amino-3-methylpentanoyl];

or mixtures thereof;

or (c) as one of the diastereomers of the formula:

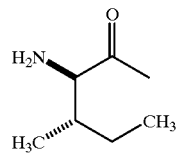

[(2R,3S)-2-amino-3-methylpentanoyl]; or

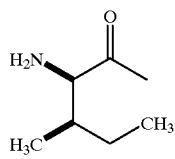

[(2R,3R)-2-amino-3-methylpentanolyl];

or mixtures thereof.

R may be $H_2N(CH_2)_4CH(NH_2)$—CO— in the form of a stereoisomeric mixture, or as one of the enantiomers, i.e., the L-form of the formula:

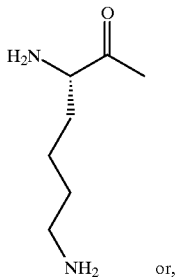

or, the D-form of the formula:

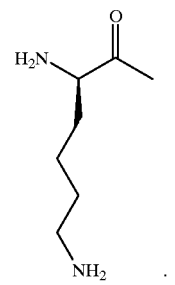

Preferably, R is L-α-aminopropanoyl of the formula:

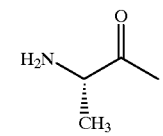

General Synthetic Preparation

Ribavirin, 1β-D-ribofuranosyl-1H-1,2,4-triazole-3-carboxamide, available from ICN Pharmaceuticals, Inc., Costa Mesa, Calif., is described in the Merck Index, compound No. 8199, Eleventh Edition. Its manufacture and formulation is described in U.S. Pat. No. 4,211,771.

Example 1

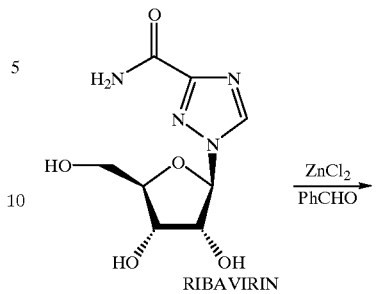

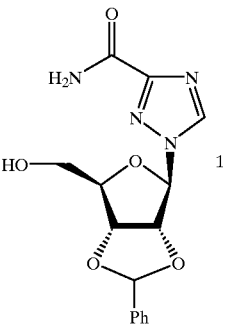

Combine 20 g ribavirin (87 mmol), 200 ml of benzaldehyde, and 20 g of $ZnCl_2$. Stir the so-formed reaction mixture at ambient temperature for 24 hours. Pour the resulting solution, with stirring, into 2.5 L of ethyl ether ($Et_2O$). Suction-filter the resulting mixture and dry the solid precipitate. Mix the solid precipitate with 1.2 L of ice-cold 2N sodium hydroxide (NaOH) solution. Extract the mixture with 2×0.75L of cold ethyl acetate (EtOAc) and wash the organic layer with brine. Gravity-filter the organic layer through fluted filter paper, then concentrate it in vacuo to leave a solid. Triturate the solid thoroughly with 0.5 L of $Et_2O$, suction-filter and wash the so-formed precipitate with fresh $Et_2O$ to leave 23 g of compound 1 as a solid; Calc. for $C_{15}H_{16}N_4O_5$ (332.32). MS(FAB)=333.1.(MH+)

Example 2

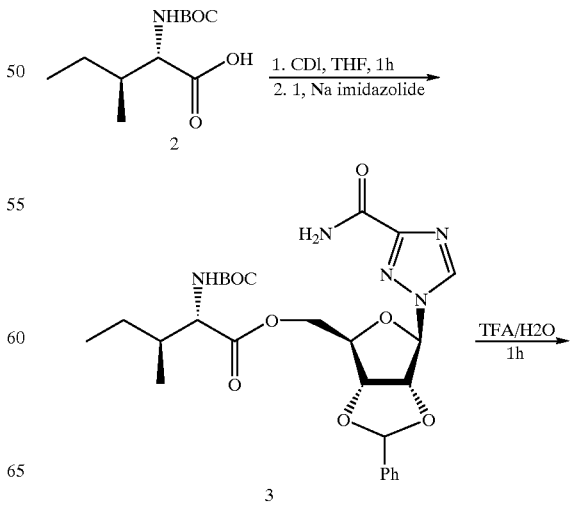

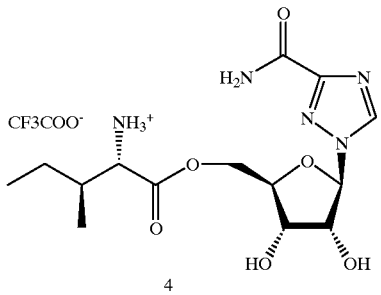

A solution of N-t-Boc-L-isoleucine (available from Sigma Chemical Co. St. Louis, Mo.) (1.270 g, 5.5 mmol) in anhydrous THF (3mL) was treated with CDI, i.e., carbonyldiimidazole (981 mg, 6.05 mmol) at room temperature for 1 hr. The compound 1 of Example 1 (1.660 g, 5.00 mmol) and sodium imidazolide (150 mg, 1.5 mmol) were then added to the reaction mixture. This mixture was heated at 45° C. for 20 hrs. The reaction was diluted with EtOAc and quenched with aqueous $NH_4Cl$. The organic layer was washed with water three times and once with brine, and dried over $Na_2SO_4$ The dried organic layer was filtered and the filtrate was concentrated to give an off white solid which was purified on silica gel column chromatography (5–10% by volume of MeOH in $CH_2Cl_2$) to afford 1.244 g of compound 3.

Compound 3 was treated with trifluoroacetic acid (TFA)/water (9:1 v/v) at room temperature for 1 hr. All volatiles were evaporated. Water was added and evaporated again to afford 1.10 g of compound 4 as a soft solid. MS(FAB)=358 ($MH^+$, 100%).

Example 3

A solution of N,N-diCbz-L-lysine (available from Sigma Chemical Co. St. Louis, Mo.) (749 mg, 1.81 mmol) and compound 1 (500 mg, 1.506 mmol) in anhydrous DMF (5 mL) was treated with (732 mg, 1.66 mmol) of benzotriazolyloxytris-(dimethylamino)phosphonium hexafluorophosphate ("BOP reagent" available from Sigma Chemical Co. St. Louis, Mo.) followed by 576 mL, 3.31 mmol of Hunig's base, i.e., N,N-diisopropyl-ethyl amine, ["(i-Pr)$_2$NEt " available from Aldrich Chemical Co., Milwaukee, Wis.] under a nitrogen atmosphere at room temperature. The reaction mixture was stirred at room temperature overnight. The reaction mixture was diluted with EtOAc and quenched with aqueous $NH_4Cl$. The organic layer was washed three times with water, once with brine, and dried over $Na_2SO_4$ and . The dried organic layer was filtered and the filtrate was concentrated to give compound 5 as an off white solid.

Compound 5 was treated with trifluoroacetic acid/water (9:1 v/v) at room temperature for 1 hr. All volatiles were evaporated. Water was added and evaporated again to afford the crude product which was purified on a silica gel column (10% by volume of MeOH in $CH_2Cl_2$ ) to afford 520 mg of compound 6 as a white solid.

A solution containing compound 6 (140 mg, 0.219 mmol) and p-toluenesulfonic acid monohydrate, TsOH $H_2O$ (83 mg, 0.438 mmol) was hydrogenated over 10% Pd/C (50 mg) under $H_2$ at a pressure of 1 atm for 4 hr. The catalyst was filtered off through a bed of Celite and washed with methanol-water. The filtrate was evaporated to afford 157 mg of compound 7 as a white powder. MS(FAB)=373 ($MH^+$, 100%).

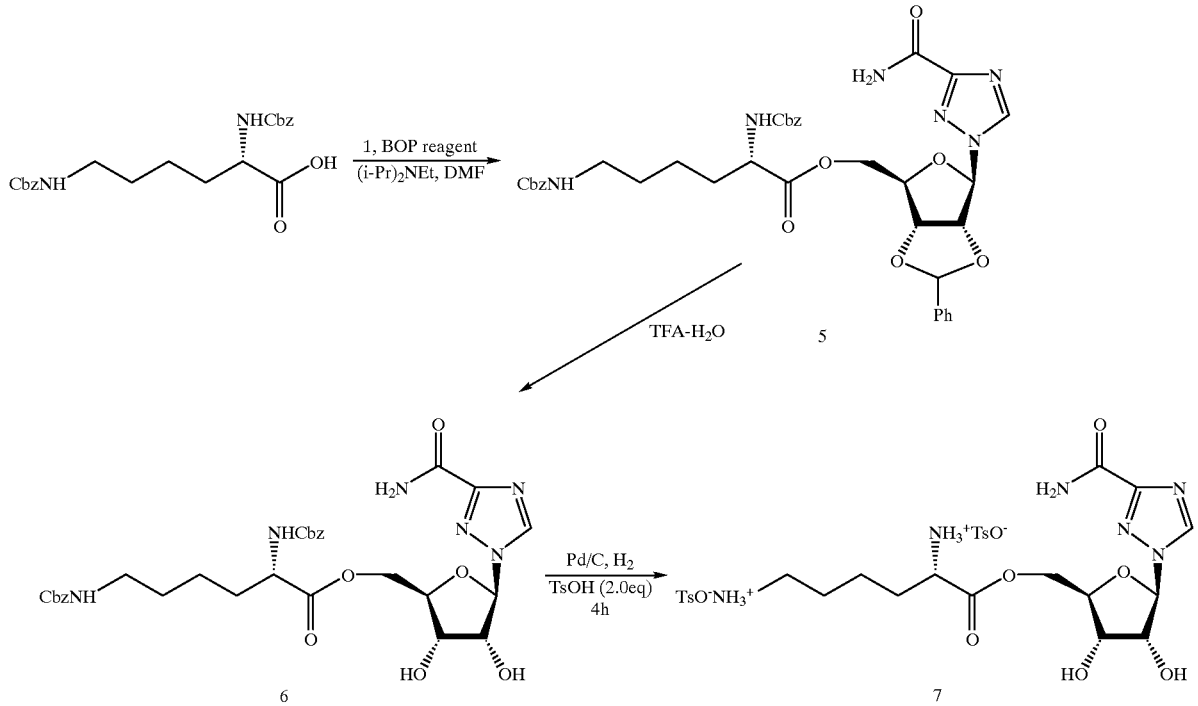

Example 4

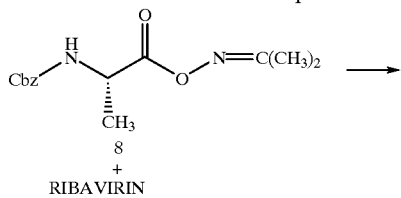
+
RIBAVIRIN

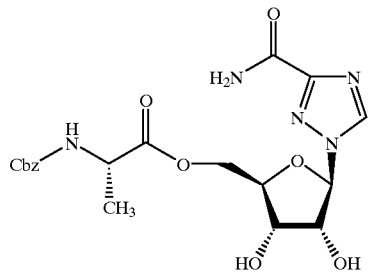

A solution of 3.6 mmol of the oxime ester of Cbz-L-alanine8 (prepared in accordance with the procedures of F. Moris & V. Gotor, Tetrahedron.1994, 50, 6927–6934 at paragraph bridging 6932–33) and 0.48g of Novo SP435 lipase (Candida Antarctica) in 12 mL of anhydrous THF was stirred at 65° C. for 24 hrs. The so-formed reaction mixture was cooled to room temperature, filtered and washed with MeOH. The combined filtrates were evaporated and the so-formed residue was purified on silica gel column chromatography using 10% MeOH/$CH_2Cl_2$ (v/v) as eluent to produce 660 mg of compound 9 as a white solid. No other product was observed by TLC. The white solid was recrystallized from MeOH-EtOAc to give 0.532 g of compound 9.

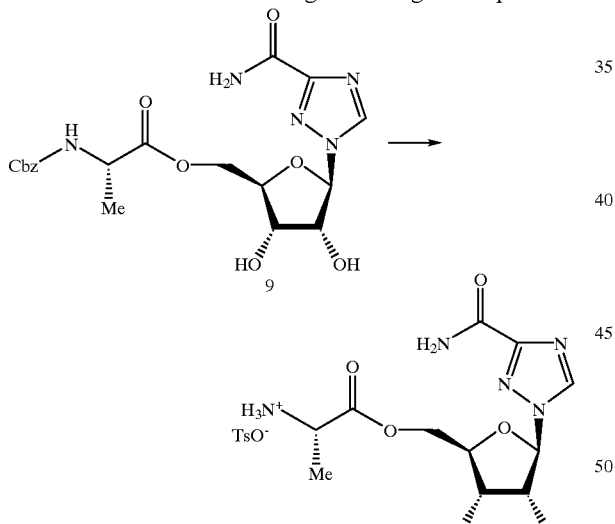

To a mixture of 0.100 g (0.222 mmol) of compound 9 and 42.3 mg (1 eq) of TsOH.$H_2O$ in 3 ml of aqueous MeOH was added 50 mg of 10% Pd on carbon. The resulting black suspension was placed under a hydrogen atmosphere for 4 hrs. The so-formed reaction mixture was filtered through a pad of celite and the solid was washed thoroughly with methanol. The combined filtrates were concentrated and the solvent removed to give 0.101 g of compound 10 as a white solid. MS (FAB)=316.1(MH+)

Example 5

Follow the procedures of Examples 2, 3, or 4 except substitute an equivalent amount of the Cbz- or Boc-D-amino acid derivative of the amino acid listed in the left hand column in the Table 3 below for the Boc-L-isoleucine used in Example 2, or the diCbz-L-lysine used in Example 3, or the Cbz-L-alanine used in Example 4 to obtain the compounds of formula I or a pharmaceutical acceptable salt thereof wherein the R is the moiety listed in the right hand column of the Table 3 below.

TABLE 3

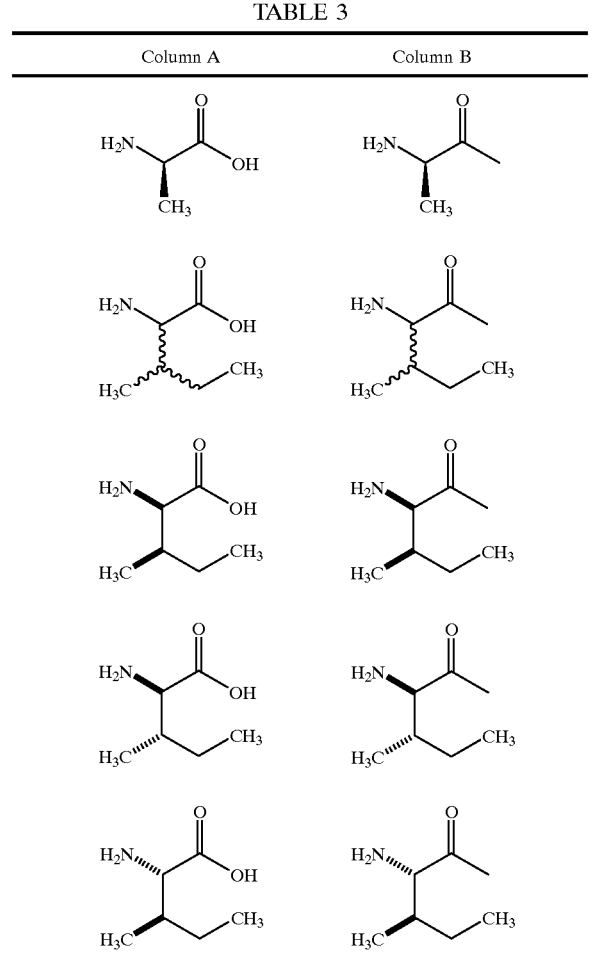

What is claimed is:
1. A compound represented by the formula I

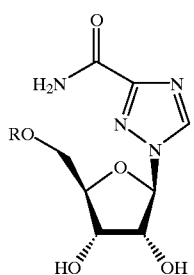

wherein R is $CH_3CH(NH_2)$—CO—, $CH_3CH_2(CH_3)CHCH(NH_2)$—CO—or
$H_2N(CH_2)_4CH(NH_2)$—CO—;
or a pharmaceutically acceptable salt thereof.
2. The compound of claim 1 wherein pharmaceutically acceptable salt is trifluoroacetate, tosylate, mesylate, or chloride.

3. The compound of claim 1 wherein R is

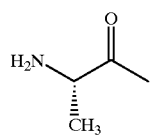

or a pharmaceutically acceptable salt thereof.

4. The compound of claim 1 wherein R is

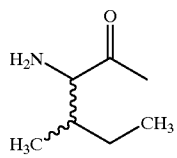

or a pharmaceutically acceptable salt thereof.

5. The compound of claim 1 wherein R is

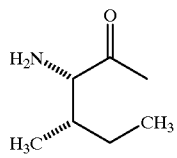

or a pharmaceutically acceptable salt thereof.

6. The compound of claim 1 wherein R is

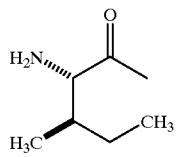

or a pharmaceutically acceptable salt thereof.

7. The compound of claim 1 wherein R is

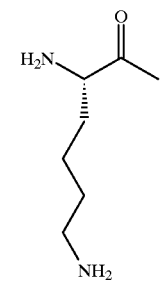

or a pharmaceutically acceptable salt thereof.

8. The compound of claim 1 wherein R is

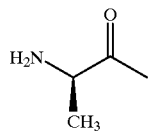

or a pharmaceutically acceptable salt thereof.

9. The compound of claim 1 wherein R is

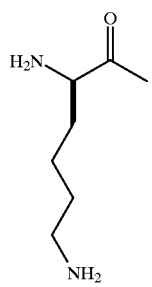

or a pharmaceutically acceptable salt thereof.

10. The compound of claim 1 wherein R is

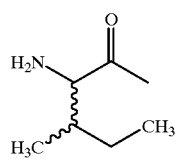

or a pharmaceutically acceptable salt thereof.

11. The compound of claim 1 wherein R is

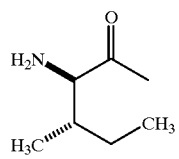

or a pharmaceutically acceptable salt thereof.

12. The compound of claim 1 wherein R is

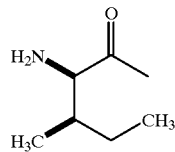

or a pharmaceutically acceptable salt thereof.

13. A pharmaceutical composition for treating susceptible viral infections comprising a compound of claim 1 and at least one pharmaceutically acceptable carrier.

14. The pharmaceutically composition of claim 12 adapted for oral administration.

15. A method of treating a patient with a susceptible viral infection which comprises administering to said patient an effective amount of a compound of claim 1.

16. A method of treating a patient infected with chronic hepatitis C which comprises administering to said patient an effective amount of a compound of formula I in association with an effective amount of an interferon alfa for a time sufficient to eradicate detectable HCV-RNA levels, wherein the compound represented by the formula I:

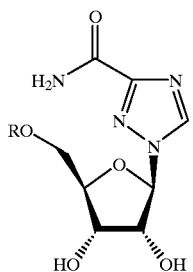

I wherein R is CH$_3$CH(NH$_2$)—CO—, CH$_3$CH$_2$(CH$_3$)CHCH(NH$_2$)—CO— or H$_2$N(CH$_2$)$_4$CH(NH$_2$)—CO—; or a pharmaceutically acceptable salt thereof.

17. The method of claim 16 wherein the pharmaceutically acceptable salt is trifluoroacetate, tosylate, mesylate, or chloride.

18. The method of claim 16 wherein R is

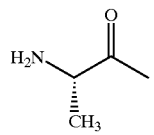

or a pharmaceutically acceptable salt thereof.

19. The method of claim 16 wherein R is

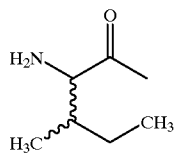

or a pharmaceutically acceptable salt thereof.

20. The method of claim 16 wherein R is

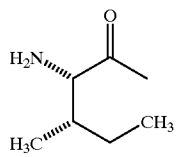

or a pharmaceutically acceptable salt thereof.

21. The method of claim 16 wherein R is

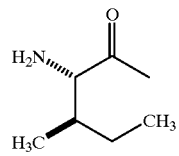

or a pharmaceutically acceptable salt thereof.

22. The method of claim 16 wherein R is

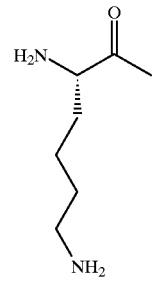

or a pharmaceutically acceptable salt thereof.

23. The method of claim 16 wherein R is

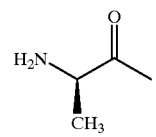

or a pharmaceutically acceptable salt thereof.

24. The method of claim 16 wherein R is

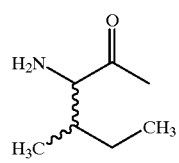

or a pharmaceutically acceptable salt thereof.

25. The method of claim 16 wherein R is

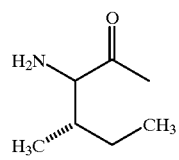

or a pharmaceutically acceptable salt thereof.

26. The method of claim 16 wherein R is

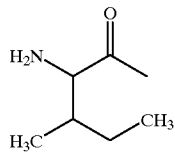

or a pharmaceutically acceptable salt thereof.

27. The method of claim 16 wherein R is

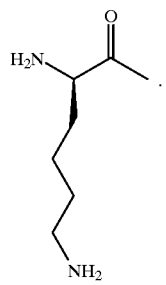

or a pharmaceutically acceptable salt thereof.

28. The method of claim 16 wherein the interferon alfa is interferon alpha-2a, interferon alpha-2b, consensus interferon, pegylated interferon alpha-2a or pegylated interferon alfa -2b.

29. The method of claim 16 wherein the compound represented by the formula I is administered orally.

30. The method of claim 16 wherein the compound represented by the formula I is administered parenterally.

31. The method of claim 16 wherein the compound represented by the formula I is administered intranasally.

32. The method of claim 16 wherein the compound represented by the formula I is administered intravenously.

33. The method of claim 16 wherein the compound represented by the formula I is administered subcutaneously.

34. The method of claim 16 wherein the compound represented by the formula I is administered intramuscularly.

35. A method of treating a patient infected with chronic hepatitis C which comprises administering to said patient an effective amount of a compound of formula II

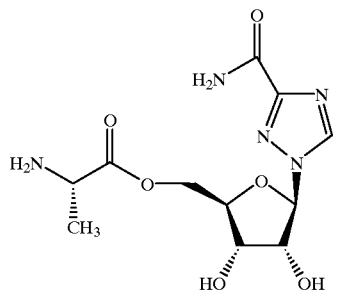

or a pharmaceutically acceptable salt thereof, in association with an effective amount of an interferon alfa for a time sufficient to eradicate detectable HCV-RNA levels.

36. The method of claim 35 wherein the interferon alfa is interferon alpha-2a, interferon alpha-2b, consensus interferon, pegylated interferon alpha-2a or pegylated interferon alfa -2b.

37. The method of claim 35 wherein the compound represented by the formula I is administered orally.

38. The method of claim 35 wherein the compound represented by the formula I is administered parenterally.

39. The method of claim 35 wherein the compound represented by the formula I is administered intranasally.

40. The method of claim 35 wherein the compound represented by the formula I is administered intravenously.

41. The method of claim 35 wherein the compound represented by the formula I is administered subcutaneously.

42. The method of claim 35 wherein the compound represented by the formula I is administered intramuscularly.

43. The method of claim 35 wherein the pharmaceutically acceptable salt is trifluoroacetate, tosylate, mesylate, or chloride.

* * * * *